(12) United States Patent
Tanihara et al.

(10) Patent No.: US 9,238,688 B2
(45) Date of Patent: Jan. 19, 2016

(54) RETINOL-MODIFIED COLLAGEN, METHOD FOR PRODUCING SAME, AND EXTERNAL COMPOSITION FOR SKIN CONTAINING SAME

(75) Inventors: Masao Tanihara, Ikoma (JP); Kana Takaichi, Takatsuki (JP); Mariko Maeda, Takatsuki (JP); Tsukasa Mitsui, Takatsuki (JP); Kazushi Yamamoto, Takatsuki (JP); Akiko Hirano, Takatsuki (JP)

(73) Assignees: NATIONAL UNIVERSITY CORPORATION NARA INSTITUTE OF SCIENCE AND TECHNOLOGY, Nara (JP); SUNSTAR INC., Osaka (JP)

( * ) Notice: Subject to any disclaimer, the term of this patent is extended or adjusted under 35 U.S.C. 154(b) by 0 days.

(21) Appl. No.: 13/703,477

(22) PCT Filed: Jun. 15, 2011

(86) PCT No.: PCT/JP2011/063704
§ 371 (c)(1),
(2), (4) Date: Dec. 11, 2012

(87) PCT Pub. No.: WO2011/158864
PCT Pub. Date: Dec. 22, 2011

(65) Prior Publication Data
US 2013/0116189 A1 May 9, 2013

(30) Foreign Application Priority Data

Jun. 15, 2010 (JP) .................................. 2010-136293

(51) Int. Cl.
| | |
|---|---|
| *C07K 14/78* | (2006.01) |
| *A61Q 19/08* | (2006.01) |
| *A61Q 19/00* | (2006.01) |
| *C07K 1/107* | (2006.01) |
| *A61K 8/67* | (2006.01) |
| *A61K 31/07* | (2006.01) |
| *A61K 38/39* | (2006.01) |
| *A61Q 1/00* | (2006.01) |
| *A61Q 1/02* | (2006.01) |
| *A61Q 1/12* | (2006.01) |
| *A61Q 5/02* | (2006.01) |
| *A61Q 5/12* | (2006.01) |
| *A61Q 19/10* | (2006.01) |

(52) U.S. Cl.
CPC ................ *C07K 14/78* (2013.01); *A61K 8/671* (2013.01); *A61K 31/07* (2013.01); *A61K 38/39* (2013.01); *A61Q 19/00* (2013.01); *A61Q 19/08* (2013.01); *C07K 1/1077* (2013.01); *A61Q 1/00* (2013.01); *A61Q 1/02* (2013.01); *A61Q 1/12* (2013.01); *A61Q 5/02* (2013.01); *A61Q 5/12* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 3,991,184 | A * | 11/1976 | Kludas et al. | ................ 514/17.2 |
| 2007/0207180 | A1 | 9/2007 | Tanihara et al. | |
| 2010/0286368 | A1 | 11/2010 | Tanihara | |

FOREIGN PATENT DOCUMENTS

| | | |
|---|---|---|
| EP | 1 859 818 A1 | 11/2007 |
| EP | 2 189 476 A1 | 5/2010 |
| JP | 8-073338 | 3/1996 |
| JP | 2009-067727 | 4/2009 |
| JP | 2009067727 A * | 4/2009 |
| WO | 94/09756 | 5/1994 |
| WO | 03/030860 | 4/2003 |
| WO | 2009/035092 | 3/2009 |

OTHER PUBLICATIONS

Sorg et al. Dermatologic Therapy. 19;289-296:2006.*
International Search Report issued Aug. 23, 2011 in International (PCT) Application No. PCT/JP2011/063704.
M. Tanihara, "Synthesis of Collagen-like Polypeptide and its Potential", Kagaku to Seibutsu, vol. 47, No. 5, pp. 339-344, 2009 (partial English translation).
International Preliminary Report on Patentability and Written Opinion issued Jan. 17, 2013 in International (PCT) Application No. PCT/JP2011/063704, with English translation.
Office Action issued Apr. 25, 2014 in corresponding Chinese Application No. 201180029580.1, with English translation.
Extended European Search Report issued Jan. 21, 2014 in corresponding European Application No. 11795768.8.

(Continued)

*Primary Examiner* — Amber D Steele
*Assistant Examiner* — Schuyler Milton
(74) *Attorney, Agent, or Firm* — Wenderoth, Lind & Ponack, L.L.P.

(57) ABSTRACT

Disclosed is a compound which exhibits a higher effect of preventing wrinkle formation, a higher effect of improving wrinkles, a higher effect of making the skin beautiful, and a higher effect of improving skin quality than conventional retinol and retinol derivatives in a sustained manner. Further disclosed are a method for producing the same, and an external composition for the skin and a sheet-shaped cosmetic each containing the same as an active ingredient. More specifically disclosed are retinol-modified collagen in which a dicarboxylic acid is attached to at least one hydroxyl group of collagen and retinol is attached to a carboxyl group of at least one attached dicarboxylic acid, a method for producing the same, and an external composition for the skin and a sheet-shaped cosmetic each containing the same as an active ingredient.

18 Claims, 7 Drawing Sheets

(56) References Cited

OTHER PUBLICATIONS

Schwartz et al., "Topical All-Trans Retinoic Acid Stimulates Collagen Synthesis In Vivo", The Journal of Investigative Dermatology, vol. 96, No. 6, pp. 975-978, Jun. 1, 1991.

Swatschek et al., "Microparticles derived from marine sponge collagen (SCMPs): preparation, characterization and suitability for dermal delivery of all-trans retinol", European Journal of Pharmaceutics and Biopharmaceutics, vol. 54, No. 2, pp. 125-133, Sep. 1, 2002.

Tanihara et al., "The biodegradability of poly(Pro-Hyp-Gly) synthetic polypeptide and the promotion of a dermal wound epithelialization using a poly(Pro-Hyp-Gly) sponge", Journal of Biomoedical Materials Research Part A, vol. 85, No. 1, pp. 133-139, Apr. 1, 2008.

Office Action dated Aug. 3, 2015 in corresponding European patent application No. 11 795 768.8.

Declaration under 37 CFR 1.132 of Akiko Hirano, Mar. 10, 2014.

Declaration under 37 CFR 1.132 of Akiko Hirano, Jun. 30, 2015.

\* cited by examiner (*: $p<0.05$、 **: $p<0.01$)

( * : p<0.05 )

```
                        SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct; Designed polynucleotide
      used as forward primer for real-time PCR of HAS2 gene

<400> SEQUENCE: 1
agtcatgtac acagccttca gagca                                               25

<210> SEQ ID NO 2
<211> LENGTH: 22
<212> TYPE: DNA
<213> ORGANISM: Artificial Sequence
<220> FEATURE:
<223> OTHER INFORMATION: Synthetic Construct; Designed polynucleotide
      used as reverse primer for real-time PCR of HAS2 gene

<400> SEQUENCE: 2
cacctccaac catgggatct tc                                                  22

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct; Designed polynucleotide
      used as forward primer for real-time PCR of HAS3 gene

<400> SEQUENCE: 3
tcggcgattc ggtggacta                                                      19

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct; Designed polynucleotide
      used as reverse primer for real-time PCR of HAS3 gene

<400> SEQUENCE: 4
cctccaggac tcgaagcatc tc                                                  22
```

RETINOL-MODIFIED COLLAGEN, METHOD FOR PRODUCING SAME, AND EXTERNAL COMPOSITION FOR SKIN CONTAINING SAME

BACKGROUND OF THE INVENTION

1. Field of the Invention

The present invention relates to retinol-modified collagen exhibiting excellent skin anti-aging effects when applied to the skin. More specifically, the present invention relates to retinol-modified collagen which has low toxicity to cells and is excellent in safety without causing itches and the like, enhances the expression of hyaluronic acid synthase genes over an extended time period and increases the production of hyaluronic acid, and also enhances the synthesis of collagen, to thereby produce an excellent effect of preventing wrinkle formation, an excellent effect of improving wrinkles, an excellent effect of making the skin beautiful and an excellent effect of improving skin quality; a method for producing the same, and an external composition for the skin and a sheet-shaped cosmetic each containing the same.

2. Description of the Related Art

Wrinkles in the skin increase as the skin ages. There are wrinkles, for example, thin horizontal wrinkles that develop as deep as the epidermis under the eyes (the epidermis wrinkles), wrinkles that develop as deep as the dermis and appear as fine creases that develop vertically to the mimic muscles in the corners of the eyes, the forehead and the like (dermis wrinkles), and wrinkles that appear as huge creases around the eyes and mouth, in the contours of the face and the like (old age wrinkles). However, there have been no countermeasures that act comprehensively on portions such as the epidermis and dermis, and that provide a multiphase solution to prevent wrinkle formation and to wrinkle improvement.

Meanwhile, collagen or its derivatives are fibrous proteins that may be found in all multicellular organisms, and incorporated in various cosmetics for the purpose of preventing skin aging.

However, conventional collagen or collagen derivatives have a problem of not being able to produce excellent and satisfactory anti skin aging effects.

Accordingly, in light of the existing problems of collagen, the inventors of the present invention have completed an invention relating to polypeptide having a collagen-like structure, and filed an application for the invention (WO 2009/035092).

On the other hand, retinol and its derivatives are a kind of vitamin known to be involved with sustaining, for example, vital functions including visual perception and reproductive functions of normal epithelium tissues such as skin and mucous membrane. They are known as pharmaceuticals for external use for dyskeratosis skin diseases such as ichthyosis vulgaris. Further, retinol derivatives are known to suppress the aging of the skin by sustaining the activities of epithelium tissues and screening the signal transmission of ultraviolet light, and they are widely used as cosmetics for preventing the skin from aging.

However, retinol conventionally reported is toxic to cells, and anti-skin aging effects exhibited by retinol derivatives can not be sustained over an extended time period. Thus, multiphase prevention or improvement of wrinkles can not be carried out. Therefore, development of more effective retinol derivatives and development of active ingredients instead of retinol or its derivatives have been desired.

SUMMARY OF THE INVENTION

Accordingly, an object of the present invention is to provide a compound which sustains, over an extended time period, a higher safety feature, a higher effect of preventing wrinkle formation, a higher effect of improving wrinkles, a higher effect of making the skin beautiful and a higher effect of improving skin quality than conventional retinol and retinol derivatives, and provides multiphase prevention or improvement of wrinkles; a method for producing the same, and an external composition for the skin and a sheet-shaped cosmetic each containing the same as an active ingredient.

The inventors of the present invention have made intensive studies to solve the problems as described above and found that a substance, which is obtained by attaching retinol to a polypeptide (fibrous aggregate) prepared by condensing peptide units each having a particular amino acid sequence, has low cell toxicity, generates no inflammatory cytokine, increases the production of hyaluronic acid in the epidermis, promotes the synthesis of collagen in the dermis, and thus is capable of exerting such excellent effects. The finding has led to completion of the present invention.

In other words, the present invention provides:

[1] a retinol-modified collagen, wherein a dicarboxylic acid is attached to at least one hydroxyl group of collagen, and retinol is attached to a carboxyl group of at least one attached dicarboxylic acid;

[2] the retinol-modified collagen according to [1], wherein the collagen is one or more kinds selected from the group consisting of natural collagen and collagen containing a peptide unit represented by formula (1):

$$-(A1-A2-Gly)- \quad (1)$$

(wherein Gly represents glycine, and A1 and A2 represent glycine, proline (Pro) or hydroxyproline (Hyp), provided that at least one of A1 and A2 is Hyp), gelatin, and a hydrolysate of natural collagen and a hydrolysate of collagen containing a peptide unit represented by formula (1);

[3] the retinol-modified collagen according to [1] or [2], wherein the dicarboxylic acid is one or more kinds selected from the group consisting of oxalic acid, malonic acid, succinic acid, glutaric acid, adipic acid, pimelic acid, suberic acid, azelaic acid, sebacic acid, phthalic acid, isophthalic acid, terephthalic acid, fumaric acid, and maleic acid;

[4] the retinol-modified collagen according to [3], wherein the dicarboxylic acid is succinic acid;

[5] the retinol-modified collagen according to any one of [1] to [4], comprising a peptide unit represented by formula (2):

[Chemical Formula 1]

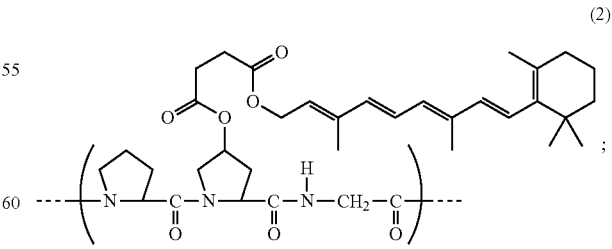

[6] the retinol-modified collagen according to any one of [1] to [4], comprising the peptide unit represented by formula (2) and at least one kind of a peptide unit represented by formula (3):

[Chemical Formula 2]

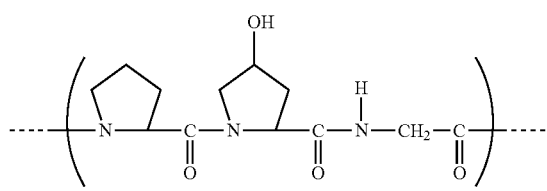

and a peptide unit represented by formula (4):

[Chemical Formula 3]

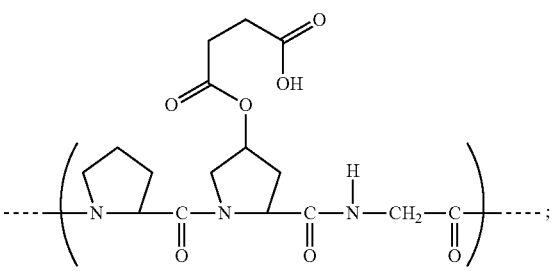

[7] the retinol-modified collagen according to [6], wherein a content ratio between the peptide unit represented by formula (2), and the peptide unit represented by formula (3) and the peptide unit represented by formula (4) is, in terms of mole ratio, in the range of (2):((3)+(4))=1:99 to 100:0;
[8] the retinol-modified collagen according to any one of [1] to [7], wherein the peak of molecular weight distribution falls within the range of molecular weight of 500 to 1,000,000;
[9] the retinol-modified collagen according to any one of [1] to [8], which is an agent for preventing wrinkle formation;
[10] the retinol-modified collagen according to any one of [1] to [9], which is a hyaluronic acid production, accelerator;
[11] the retinol-modified collagen according to any one of [1] to [10], which is an activating agent for hyaluronic acid synthase;
[12] the retinol-modified collagen according to any one of [1] to [11], wherein the retinol-modified collagen is a collagen production accelerator;
[13] a method for producing the retinol-modified collagen according to [1], comprising:
  (1) preparing dicarboxylic acid-conjugated collagen by attaching a dicarboxylic acid or its anhydride to at least one hydroxyl group of collagen; and then
  (2) attaching retinol to a carboxyl group of the dicarboxylic acid of the dicarboxylic acid-conjugated collagen;
[14] the method for production according to [13], wherein the collagen is one or more kinds selected from the group consisting of natural collagen and collagen containing a peptide unit represented by formula (1):

-(A1-A2-Gly)-  (1)

(wherein Gly represents glycine, and A1 and A2 represent glycine, praline (Pro) or hydroxyproline (Hyp), provided that at least one of A1 and A2 is Hyp), gelatin, and a hydrolysate of natural collagen and a hydrolysate of collagen containing a peptide unit represented by formula (1);
[15] the method for production according to [13] or [14], wherein the dicarboxylic acid is one or more kinds selected from the group consisting of oxalic acid, malonic acid, succinic acid, glutaric acid, adipic acid, pimelic acid, suberic acid, azelaic acid, sebacic acid, phthalic acid, isophthalic acid, terephthalic acid, fumaric acid, and maleic acid;
[16] the method for production according to [15], wherein the dicarboxylic acid is succinic acid;
[17] the method for production according to any one of [13] to [16], wherein a tertiary amine is used as a solvent in step (2);
[18] the method for production according to [17], wherein the tertiary amine is a trialkylamine;
[19] the method for production according to [18], wherein the trialkylamine is diisopropylethylamine;
[20] an external composition for the skin comprising, as an active ingredient, the retinol-modified collagen according to any one of [1] to [12];
[21] an external composition for the skin comprising the retinol-modified collagen according to any one of [1] to [12] in an amount of 0.00001 to 30% by weight based on the total amount of the composition;
[22] the external composition for the skin according to [20] or [21], which is used for preventing wrinkle formation;
[23] a sheet-shaped cosmetic comprising the retinol-modified collagen according to any one of [1] to [12].

The novel retinol-modified collagen of the present invention is excellent in a safety feature, in compatibility to the skin and act on the skin in a sustained manner to continuously exert an excellent and multiphase effect of preventing wrinkle formation, an excellent and multiphase effect of improving wrinkles, an excellent and multiphase effect of making the skin beautiful and an excellent and multiphase effect of improving skin quality. Such retinol-modified collagen may be suitably used, in a single compound, as an agent for preventing wrinkle formation, agent for improving wrinkles, an agent for making the skin beautiful, an agent for improving skin quality, an agent for promoting hyaluronic acid production, an agent for activating hyaluronic acid synthase and an agent for promoting collagen production. Moreover, the retinol-modified collagen is suitable for use as an active ingredient of external compositions for the skin, for example, external compositions for the skin for preventing wrinkle formation, improving wrinkles, making the skin beautiful, and improving skin quality, sheet-shaped cosmetics and the like.

DETAILED DESCRIPTION OF THE INVENTION

Figure 1A:
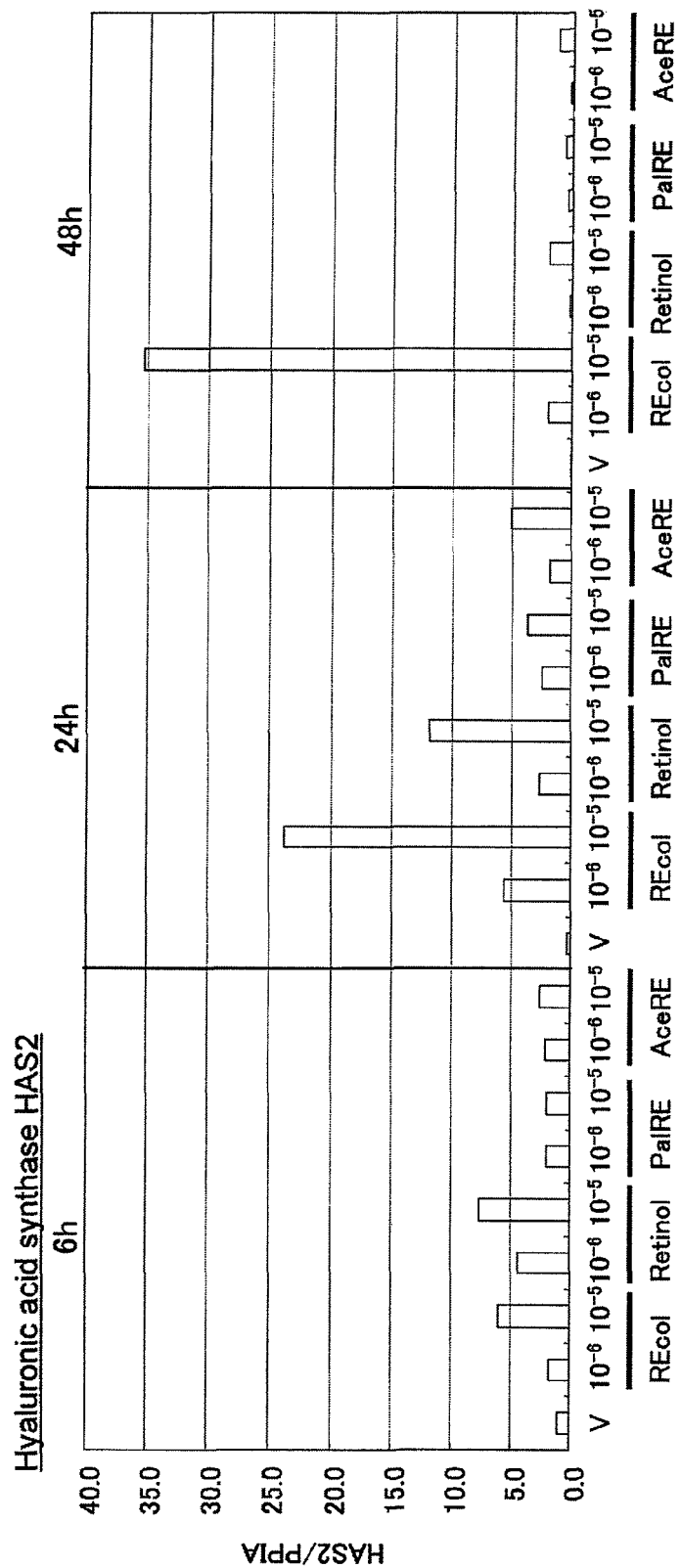
FIG. 1A is a figure showing an effect produced by the retinol-modified collagen of the present invention and an effect produced by conventional retinol derivatives on the expression of hyaluronic acid synthase genes (HAS2) (Experimental Example 1).

In a first aspect, the present invention provides novel retinol-modified collagen.

The retinol-modified collagen of the present invention is collagen in which retinol is esterified via a dicarboxylic acid with at least one hydroxyl group of an amino acid residue constituting the collagen.

Examples of collagen constituting the retinol-modified collagen of the present invention include natural collagen, collagen containing a peptide unit represented by formula (1):

-(A1-A2-Gly)-    (1)

(wherein Gly represents glycine, and A1 and A2 represent glycine, proline (Pro) or hydroxyproline (Hyp), provided that at least one of A1 and A2 is Hyp), gelatin, and a hydrolysate of natural collagen and a hydrolysate of collagen containing a peptide unit represented by formula (1).

Of these kinds, collagen containing a peptide unit represented by formula (1) (hereinafter, referred to as "synthetic collagen") may be prepared by dissolving one or more kinds of peptide units selected from Gly-Hyp-Gly-, Pro-Hyp-Gly-, Hyp-Gly-Gly- and Hyp-Pro-Gly- in a suitable buffer solution, adding a condensation aid such as 1-hydroxybenzotriazole (HOBt) to the resulting solution, further adding a dehydration condensation agent such as 1-ethyl-3-(3-dimethylaminopropyl)-carbodiimide hydrochloride under cooling to the resulting solution, and dialyzing the reaction solution obtained by agitating the resulting solution against water or a suitable buffer solution.

The condensation reaction of the synthetic collagen that may be used in the present invention can be carried out in a solvent that is capable of dissolving or suspending (dissolving the whole or a portion of) the peptide unit as described above, and usually a buffer solution may be used. Examples of the buffer solution that may be used include a phosphate buffer solution, a carbonate buffer solution and the like. Moreover, a non-aqueous solvent that does not contain water may also be used.

Examples of the condensation aid that may be used in the condensation reaction of the synthetic collagen include, besides N-hydroxytriazoles such as 1-hydroxybenzotriazole (HOBt) as described above, N-hydroxy polyvalent carboxylic acid imides [for example, N-hydroxydicarboxylic acid imides such as N-hydroxysuccinimide (HONSu) and N-hydroxy-5-norbornene-2,3-dicarboxylic acid imide (HONB)], triazines such as 3-hydroxy-4-oxo-3,4-dihydro-1,2,3-benzotriazine (HOObt), a 2-hydroxyimino-2-cyanoacetic acid ethyl ester, and the like. These condensation aids may be used independently or in combination of two or more kinds thereof. Preferable condensation aids are N-hydroxybenzotriazoles such as 1-hydroxybenzotriazole (HOBt).

The amount of the condensation aid to be used is, for example, about 0.05 to 5 moles, preferably about 0.1 to 2 moles, and more preferably about 0.15 to 1 mole based on 1 mole of the peptide unit regardless of the kind of an aqueous or non-aqueous solvent.

Examples of the dehydration condensation agent that may be used in the condensation reaction of the synthetic collagen include, besides 1-ethyl-3-(3-dimethylaminopropyl)-carbodiimide hydrochloride (WSCI.HCl) as described above, carbodiimide-based condensation agents [such as diisopropyl-carbodiimide (DIPC), 1-ethyl-3-(3-dimethylaminopropyl)-carbodiimide (EDC=WSCI), and dicyclohexylcarbodiimide (DCC)], fluorophosphate-based condensation agents [such as O-(7-azabenzotriazol-1-yl)-1,1,3,3-tetramethyluronium hexafluorophosphate, O-benzotriazol-1-yl-N,N,N',N'-tetramethyluronium hexafluorophosphate, benzotriazol-1-yl-oxy-tris-pyrrolidinophosphonium hexafluorophosphate, and benzotriazol-1-yl-tris(dimethylamino)phosphonium hexafluorophosphide (BOP)], diphenylphosphoryl azide (DPPA), and the like. These dehydration condensation agents may be used independently or in combination of two or more kinds thereof. Preferable dehydration condensation agents are carbodiimide-based condensation agents such as 1-ethyl-3-(3-dimethylaminopropyl)-carbodiimide hydrochloride.

Because the dehydration condensation agent is deactivated by water, the amount of the dehydration condensation agent to be used, when an aqueous solvent containing water is used, is generally about 2 to 500 moles (for example, about 2 to 50 moles), preferably about 5 to 250 moles (for example, about 5 to 25 moles), and more preferably about 10 to 125 moles (for example, about 10 to 20 moles) based on 1 mole of the peptide unit. On the other hand, when a non-aqueous solvent which does not contain water is used, the amount of the dehydration condensation agent to be used is about 0.7 to 5 moles, preferably about 0.8 to 2.5 moles, and more preferably about 0.9 to 2.3 moles (for example, about 1 to 2 moles).

In the condensation reaction in producing the synthetic collagen, the pH of the reaction system may be adjusted, or a base that is not involved in the reaction may be added. The adjustment of the pH may be usually carried out by using an inorganic base [such as sodium hydroxide, potassium hydroxide, sodium carbonate, or sodium hydrogen carbonate], an organic base, an inorganic acid [such as hydrochloric acid], or an organic acid, and the reaction solution is usually adjusted to a near neutral condition (pH of about 6 to 8). Examples of the base that is not involved in the reaction include tertiary amines, for example, trialkylamines such as trimethylamine, triethylamine, and diisopropylethylamine; heterocyclic tertiary amines such as N-methylmorpholine and pyridine; and the like. The amount of the base to be used is usually about 1 to 2 times as much as the total moles of the peptide unit.

The dicarboxylic acid constituting the retinol-modified collagen of the present invention is not particularly limited as long as it is a compound having two carboxyl groups. Examples thereof include oxalic acid, malonic acid, succinic acid, glutaric acid, adipic acid, pimelic acid, suberic acid, azelaic acid, sebacic acid, phthalic acid, isophthalic acid, terephthalic acid, fumaric acid and maleic acid, and anhydrides thereof. Preferred are malonic acid, succinic acid and glutaric acid, and anhydrides thereof, and more preferred are succinic acid and an anhydride thereof.

The retinol-modified collagen of the present invention includes not only collagen in which any one kind of the dicarboxylic acids as described above is attached to a hydroxyl group of collagen, but also collagen in which two or more kinds of the dicarboxylic acids are attached to each of the different hydroxyl groups of collagen, respectively.

In the retinol-modified collagen of the present invention, one of the two carboxyl groups of the dicarboxylic acid esterifies with a hydroxyl group of collagen.

Moreover, the retinol-modified collagen of the present invention includes from collagen in which a dicarboxylic acid is attached to one of the hydroxyl groups of collagen to collagen in which a dicarboxylic acid is attached to all the hydroxyl groups.

Retinol constituting the retinol-modified collagen of the present invention is, as described above, retinol in which retinol is esterified via a hydroxyl group with another carboxyl group of a dicarboxylic acid which is esterified with collagen.

The retinol-modified collagen of the present invention includes from collagen in which retinol is attached to one dicarboxylic acid of the dicarboxylic acids attached to collagen to collagen in which retinol is attached to all the dicarboxylic acids.

In a preferable embodiment, the retinol-modified collagen of the present invention includes retinol-modified collagen comprising a peptide unit represented by formula (2):

[Chemical Formula 4]

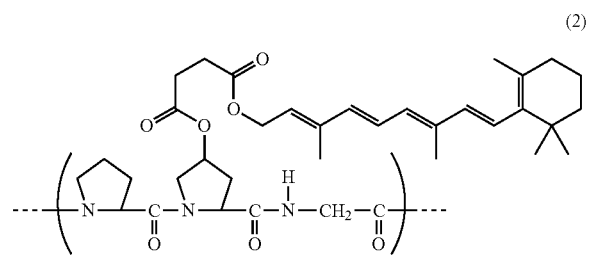

(2)

In another preferable embodiment, the retinol-modified collagen of the present invention includes retinol-modified collagen comprising the peptide unit represented by formula (2) and at least one kind of a peptide unit represented by formula (3):

[Chemical Formula 5]

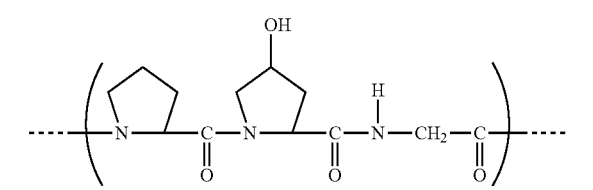

(3)

and a peptide unit represented by formula (4):

[Chemical Formula 6]

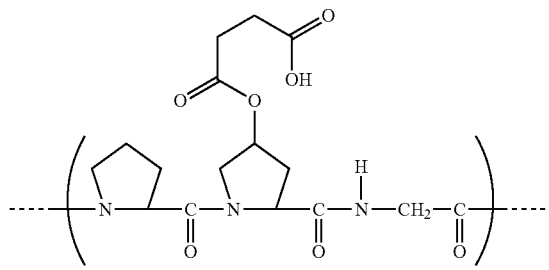

(4)

A content ratio between the peptide unit represented by formula (2), and at least one kind of a peptide unit of the peptide unit represented by formula (3) and the peptide unit represented by formula (4), each constituting the retinol-modified collagen of the present invention, namely, (2):(3), (2):(4) or (2):((3)+(4)) is, in terms of mole ratio, in the range of about 0.1:99.9 to about 100:0, about 0.3:99.7 to about 100:0, about 0.5:99.5 to about 100:0, about 1.0:99.0 to about 100:0, about 3.0:97.0 to about 100:0, about 0.1:99.9 to about 99.9:0.1, about 0.3:99.7 to about 99.9:0.1, about 0.5:99.5 to about 99.9:0.1, about 1.0:99.0 to about 99.9:0.1, about 3.0: 97.0 to about 99.9:0.1, about 0.1:99.9 to about 99.7:0.3, about 0.3:99.7 to about 99.7:0.3, about 0.5:99.5 to about 99.7:0.3, about 1.0:99.0 to about 99.7:0.3, about 3.0:97.0 to about 99.7:0.3, about 0.1:99.9 to about 99.5:0.5, about 0.3:99.7 to about 99.5:0.5, about 0.5:99.5 to about 99.5:0.5, about 1.0: 99.0 to about 99.5:0.5, about 3.0:97.0 to about 99.5:0.5, about 0.1:99.9 to about 99.0:1.0, about 0.3:99.7 to about 99.0:1.0, about 0.5:99.5 to about 99.0:1.0, about 1.0:99.0 to about 99.0:1.0, about 3.0:97.0 to about 99.0:1.0, about 0.1:99.9 to about 97.0:3.0, about 0.3:99.7 to about 97.0:3.0, about 0.5: 99.5 to about 97.0:3.0, about 1.0:99.0 to about 97.0:3.0 and about 3.0:97.0 to about 97.0:3.0; preferably about 0.1:99.9 to about 100:0, about 0.3:99.7 to about 100:0, about 0.5:99.5 to about 100:0, about 1.0:99.0 to about 100:0 and about 3.0:97.0 to about 100:0; more preferably about 0.5:99.5 to about 100: 0, about 1.0:99.0 to about 100:0 and about 3.0:97.0 to about 100:0; and most preferably about 1.0:99.0 to about 100:0.

When the content ratio of peptide unit (2) to peptide unit (3), (4) or peptide units (3)+(4), in terms of mole ratio, is less than about 0.1:99.9, an excellent effect of preventing wrinkle formation, an excellent effect of improving wrinkles, an excellent effect of making the skin beautiful and an excellent effect of improving skin quality will not be produced, and thus it is not preferable.

The retinol-modified collagen of the present invention has a peak of molecular weight in the range of, as a molecular weight, about 500 to about 3,000,000, about 1,000 to about 3,000,000, about 3,000 to about 3,000,000, about 5,000 to about 3,000,000, about 10,000 to about 3,000,000, about 30,000 to about 3,000,000, about 500 to about 2,000,000, about 1,000 to about 2,000,000, about 3,000 to about 2,000,000, about 5,000 to about 2,000,000, about 10,000 to about 2,000,000, about 30,000 to about 2,000,000, about 500 to about 1,000,000, about 1,000 to about 1,000,000, about 3,000 to about 1,000,000, about 5,000 to about 1,000,000, about 10,000 to about 1,000,000, about 30,000 to about 1,000,000, about 500 to about 700,000, about 1,000 to about 700,000, about 3,000 to about 700,000, about 5,000 to about 700,000, about 10,000 to about 700,000, about 30,000 to about 700,000, about 500 to about 500,000, about 1,000 to about 500,000, about 3,000 to about 500,000, about 5,000 to about 500,000, about 10,000 to about 500,000, about 30,000 to about 500,000, about 500 to about 100,000, about 1,000 to about 100,000, about 3,000 to about 100,000, about 5,000 to about 100,000, about 10,000 to about 100,000 and about 30,000 to about 100,000; preferably has a peak of molecular weight in the range of about 500 to about 3,000,000, about 500 to about 2,000,000, about 500 to about 1,000,000, about 500 to about 700,000, about 500 to about 500,000 and about 500 to about 100,000; and most preferably has a peak of molecular weight in the range of about 500 to about 1,000,000.

The molecular weight of the retinol-modified collagen of the present invention may be measured by, for example, gel permeation chromatography.

The retinol-modified collagen of the present invention preferably has an infrared spectrum absorption of about 1700 to 1800 $cm^{-1}$ derived from dicarboxylic acid ester bond, an UV absorption of about 300 to 350 nm derived from retinol, a peak near about 1 to 2 ppm in $^1$H-NMR derived from the cyclic structure of retinol, and a peak near about 5.5 to 7 ppm derived from the polyene structure of retinol. When the infrared spectrum absorption peak or the UV absorption peak in the ranges is small, the amount of a dicarboxylic acid attached to the main chain of collagen, or the amount of retinol attached to the dicarboxylic acid is small. The infrared spectrum absorption may be measured by FT-IR (KBr method).

The amount of the dicarboxylic acid to be attached in the retinol-modified collagen of the present invention may be measured, for example, by the peak strength ratio between an ester and an amide in the infrared spectrum absorption. It may be measured in more detail by quantifying the amount (mole number) of unreacted dicarboxylic acid with HPLC after an addition reaction of the dicarboxylic acid. That is, the amount obtained by subtracting the amount of unreacted dicarboxylic acid from the entire amount of the dicarboxylic acid used in the synthesis is the amount of the dicarboxylic acid to be attached.

The amount of retinol to be attached in the retinol-modified collagen of the present invention may be measured, for example, quantifying the amount (mole number) of unreacted retinol with HPLC after an addition reaction of the retinol. That is, the amount obtained by subtracting the amount of unreacted retinol from the entire amount of the retinol used in the synthesis is the amount of the retinol to be attached.

The retinol-modified collagen of the present invention has high compatibility to the skin, and firmly adsorbs to and permeates the skin when applied to the skin, sustainably enhances the expression of enzyme genes of the hyaluronic acid synthetic pathway and increases the production of hyaluronic acid, and by prompting the synthesis of collagen, an excellent and multiphase effect of preventing wrinkle formation, an excellent and multiphase effect of improving wrinkles, an excellent and multiphase effect of making the skin beautiful and an excellent and multiphase effect of improving skin quality are sustainably and cumulatively exerted.

Accordingly, the retinol-modified collagen of the present invention may be useful as an agent for preventing wrinkle formation, an agent for improving wrinkles, an agent for making the skin beautiful, an agent for improving skin quality, an agent for promoting hyaluronic acid production, an agent for activating hyaluronic acid synthase and an agent for promoting collagen production.

In a second aspect, the present invention provides a method for producing the retinol-modified collagen as described above.

The method of producing the retinol-modified collagen of the present invention comprises:
(1) preparing dicarboxylic acid-conjugated collagen by attaching a dicarboxylic acid or its anhydride to a hydroxyl group of collagen; and then (2) esterifying the hydroxyl group(s) of retinol with a carboxyl group of the dicarboxylic acid of the dicarboxylic acid-conjugated collagen.

The method for producing the retinol-modified collagen of the present invention uses the collagen, the dicarboxylic acid and its anhydride, and the retinol as described in the retinol-modified collagen.

The attachment of dicarboxylic acid or its anhydride to collagen may be carried out by a publicly-known method in itself using the solvent, the dehydration condensation agent and the condensation aid as described in the synthetic collagen.

An addition reaction to dicarboxylic acid-conjugated collagen is usually carried out under the condition of adding 1 or 2 equivalent amount of DIPEA based on one mole of the peptide unit to DMF (dimethylformamide) or the like. Then, a reaction to attach retinol to dicarboxylic acid-conjugated collagen was carried out under the condition as described above; however, it was found that addition of retinol thereto was hardly occurred. Surprisingly, when a tertiary amine was used as a solvent in the step of attaching retinol to a dicarboxylic acid group, it was found that the amount of retinol for addition was increased. Examples of the tertiary amine include preferably trialkylamines, and more preferably diisopropylethylamine.

The retinol-modified collagen of the present invention is excellent in compatibility to the skin as compared to conventional retinol or its derivatives, and can act on the skin in a sustained manner to continuously exert an excellent and multiphase effect of preventing wrinkle formation, an excellent and multiphase effect of improving wrinkles, an excellent and multiphase effect of making the skin beautiful and an excellent and multiphase effect of improving skin quality.

Accordingly, the present invention provides, in a further aspect, an external composition for the skin and a sheet-shaped cosmetic each containing the retinol-modified collagen as an active ingredient.

The amount of the retinol-modified collagen to be incorporated in the external composition for the skin of the present invention is about $1\times10^{-6}$ to 50 wt %, about $1\times10^{-5}$ to 50 wt %, about $5\times10^{-4}$ to 50 wt %, about $1\times10^{-4}$ to 50 wt %, about $5\times10^{-3}$ to 50 wt %, about 0.001 to 50 wt %, about $1\times10^{-6}$ to 40 wt %, about $1\times10^{-5}$ to 40 wt %, about $5\times10^{-4}$ to 40 wt %, about $1\times10^{-4}$ to 40 wt %, about $5\times10^{-3}$ to 40 wt %, about 0.001 to 40 wt %, about $1\times10^{-6}$ to 30 wt %, about $1\times10^{-5}$ to 30 wt %, about $5\times10^{-4}$ to 30 wt %, about $1\times10^{-4}$ to 30 wt %, about $5\times10^{-3}$ to 30 wt %, about 0.001 to 30 wt %, about $1\times10^{-6}$ to 20 wt %, about $1\times10^{-5}$ to 20 wt %, about $5\times10^{-4}$ to 20 wt %, about $1\times10^{-4}$ to 20 wt %, about $5\times10^{-3}$ to 20 wt %, about 0.001 to 20 wt %, about $1\times10^{-6}$ to 10 wt %, about $1\times10^{-5}$ to 10 wt %, about $5\times10^{-4}$ to 10 wt %, about $1\times10^{-4}$ to 10 wt %, about $5\times10^{-3}$ to 10 wt % or about 0.001 to 10 wt %, and preferably about $1\times10^{-5}$ to 30 wt %, based on the total amount of compositions impregnated in the external composition for the skin. When the amount to be incorporated is less than about $1\times10^{-6}$ wt %, intended effects of the present invention may not be sufficiently produced, and on the other hand, when an amount of more than 50 wt % is added, improvements in the effects corresponding to the increment cannot be obtained.

The external composition for the skin of the present invention may be formulated into pharmaceuticals such as ointments and creams, basic cosmetics such as facial cleansers, emulsions, creams, lotions, gels and liquid cosmetics, and makeup cosmetics such as foundations and lipsticks. The sheet-shaped cosmetic of the present invention may be composed of the retinol-modified collagen alone, or it may be composed of other arbitrary ingredients that may be appropriately incorporated in addition to the retinol-modified collagen. It may be formulated into facial packs, facial masks and the like.

Formulation of the external composition for the skin or the sheet-shaped cosmetic each containing the retinol-modified collagen as an active ingredient may be carried out by incorporating a solvent, a surfactant, an oil agent, a perfume material, a pigment, an anti-oxidation agent, a preservative, a colorant and the like that are well-known in the art according to a method well-known in itself.

EXAMPLES

The present invention will now be described in more detail by way of examples; however, the examples are provided for the purpose of illustration, and are not intended to limit the invention to the examples. It should be noted that "%" represents "wt %" unless otherwise specified.

Preparation Example

Synthesis of Retinol-Modified Collagen (1) Synthetic Reaction of Poly (Pro-Hyp-Gly)

After dissolving Pro-Hyp-Gly (PHG) tripeptide (PEPTIDE INSTITUTE INC.) in a 10 mM phosphate buffer solution (pH of 7.4) and agitating the solution, 1-hydroxybenzotriazole (HOBt) was added to the solution, and the resulting solution was agitated and was cooled to 5° C. or below. Then, 1-ethyl-3-(3-dimethylaminopropyl)carbodiimide hydrochloride was added to the resulting solution and was left still (reaction) for 90 minutes followed by heating up to 20° C. The reaction was then terminated by adding a 10 mM phosphate buffered saline (PBS; pH 7.4, containing 0.15M NaCl) to the resulting solution. After the reaction solution was dialyzed, the reactant was freeze dried to obtain sponge-like synthetic collagen.

(2) Assessment of Poly (Pro-Hyp-Gly) Synthesis Substance

The molecular weight of the synthesized collagen (poly-PHG) thus prepared was measured by gel permeation chromatography (GE Healthcare Japan Corporation, AKTA purifier system, column: Superdex 200HRGL, flow rate: 0.5 mL/minute, eluent: 10 mM phosphate buffered saline (PBS; pH 7.4, containing 0.15M NaCl)). As a result, it was confirmed that the molecular weight of the synthetic collagen was distributed in the range of 2,000 to 100,000 and the peak top was near 20,000. The molecular weight was calculated by using polyethylene glycol (Fluka) as a reference material.

Moreover, the circular dichroism spectrum of the synthetic collagen thus obtained was measured, and a positive Cotton effect at 225 nm and a negative Cotton effect at 197 nm were observed. It was also confirmed that a triple-helical structure had been formed.

(3) Addition Reaction of Succinic Acid to Synthetic Collagen (poly-PHG)

The dried synthetic collagen was cut into small pieces, and the pieces were washed with dimethylformamide (DMF). DMF was added and the resultant solution was cooled to 5° C. or below while agitating the solution. After adding succinic anhydride (special grade reagent, Wako Pure Chemical Industries, Ltd.) purified by recrystallization from isopropanol and diisopropylethylamine (DIPEA), the solution was allow to react for 2 hours. Then, the temperature of the resulting solution was kept at 20° C. and the resulting solution was allowed to react for another one night. The reaction was terminated by diluting the solution with water to 4 times its original volume. After the reaction solution was dialyzed, the reactant was freeze dried to obtain sponge-like synthetic collagen with addition of succinic acid thereto.

(4) Assessment of Succinic Acid-Conjugated Synthetic Collagen

An infrared absorption spectrum of the succinic acid-conjugated synthetic collagen thus prepared was measured by FT-IR (KBr method). As a result, an absorption derived from an ester bond appeared near 1730 $cm^{-1}$, and it was confirmed that the succinic acid-conjugated synthetic collagen thus obtained had a structure in which succinic acid was esterified with hydroxyl group(s) of the synthetic collagen.

(5) Addition Reaction of Retinol to Succinic Acid-Conjugated Synthetic Collagen

Dimethylformamide was added to the succinic acid-conjugated synthetic collagen to suspend. Then, N-hydroxysuccinimide (HOSu) and 1-ethyl-3-(3-dimethylaminopropyl)-carbodiimide hydrochloride were added to the resulting solution and the solution was agitated, and was allowed to react at 20° C. for one night. After washing the reactant with methanol and tetrahydrofuran, diisopropylethylamine (DIPEA) was added as a reaction solvent. Then, retinol was added to the resulting solution and was allowed to react while agitating the solution at 20° C. for one night. After washing with isopropanol and benzene, the reactant was freeze dried to obtain retinol-modified collagen of interest.

(6) Assessment of Retinol-Modified Collagen

The reactant thus obtained was dissolved in a deuterated solvent, and the $^1$H-NMR spectrum thereof was measured (JEOL, JNM-ECP 600 spectrometer). As a result, a peak derived from the cyclic structure of retinol at 1 to 2 ppm, and a peak derived from the polyene structure of retinol at 5.5 to 7 ppm were confirmed. Moreover, a hydrogen peak derived from the C15 of retinol was shifted to the lower magnetic field side as compared to that of a free retinol. Accordingly, it was confirmed that the reactant thus obtained had a structure of addition of retinol to the succinic acid-conjugated synthetic collagen via an ester bond.

Moreover, the UV absorption of the reactant thus obtained at 325 nm derived from retinol was observed, and addition of retinol was confirmed.

Experimental Example 1

Assessment of Effect Affected on Expression of Hyaluronic Acid Synthase Genes

Assessment of Retinol-Modified Collagen Using Keratinocyte Monolayer Culture System 1 (Comparisons with Retinol and Retinol Derivatives)

Human epidermal keratinocytes (Cell Application Inc.) were seeded in a 24-well plate containing a human epidermal keratinocytes growth medium (Cell Application Inc.) so that the number of cells contained in a well was $1.5 \times 10^5$, and were cultured under the condition of 5% $CO_2$-95% air and at 37° C. for about two days until the cells reached confluence.

Then, the medium was discarded, and a medium prepared to have a final retinol concentration of $10^{-6}$ M or $10^{-5}$ M, and containing the retinol-modified collagen (REcol) in the preparation example, retinol (Retinol), palmitic acid retinol ester (PalRE) or acetic acid retinol ester (AceRE), or a medium alone (control, V) was added and cultured under the condition of 5% $CO_2$-95% air and at 37° C. for 6, 24 or 48 hours. Meanwhile, each tested substance was dissolved in a small amount of dimethylformamide and added to the medium, and the concentration of dimethylformamide in all experiments was adjusted to 0.1 wt %.

After culturing for a given time period, the keratinocytes were recovered and RNA was extracted therefrom. Then, the gene expression of hyaluronic acid synthases HAS2 and HAS3 were assessed by real-time PCR using the following primer pairs (Takara Bio Inc.):

```
HAS2:
Fw Primer
                                  (SEQ. ID. No: 1)
agtcatgtacacagccttcagagca Rv Primer
                                  (SEQ. ID. No: 2)
cacctccaaccatgggatcttc HAS3:
Fw Primer
                                  (SEQ. ID. No: 3)
tcggcgattcggtggacta Rv Primer
                                  (SEQ. ID. No: 4)
cctccaggactcgaagcatctc.
```

Figure 1B:
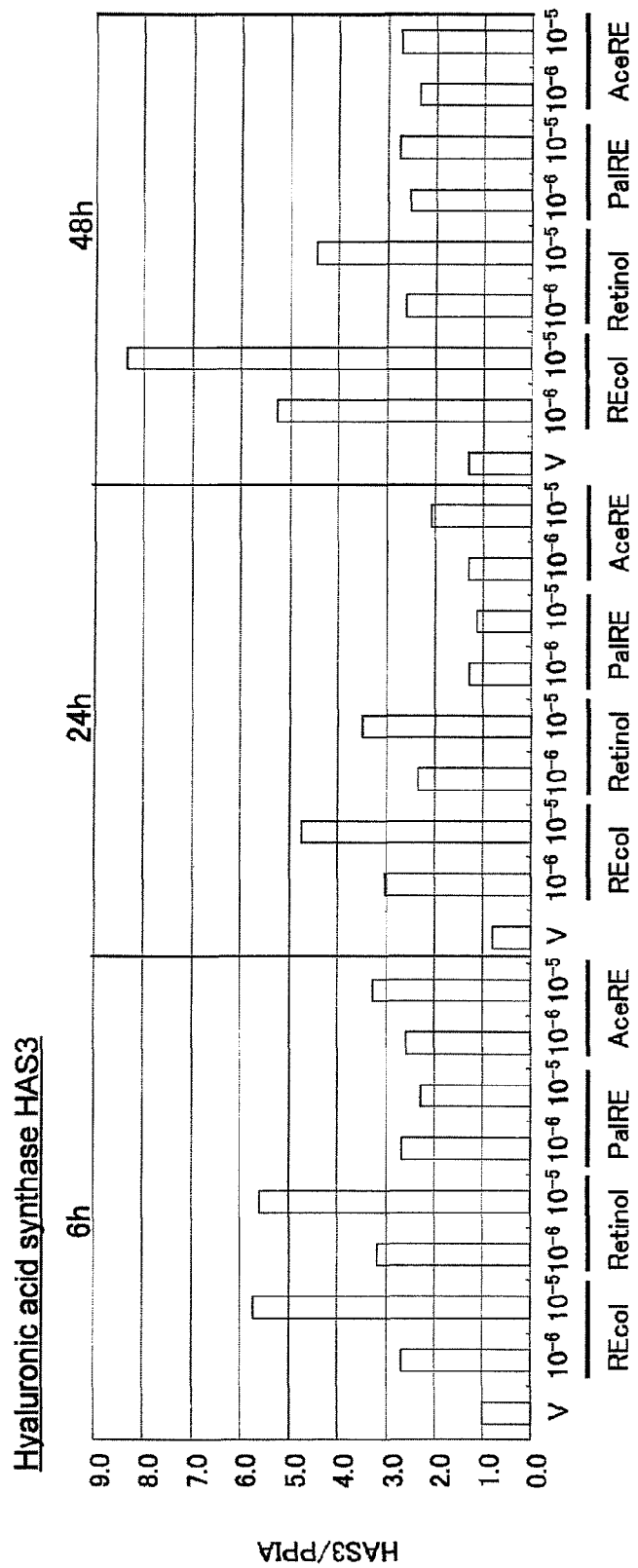
FIG. 1B is a figure showing an effect produced by the retinol-modified collagen of the present invention and an effect produced by conventional retinol derivatives on the expression of hyaluronic acid synthase genes (HAS3) (Experimental Example 1).

The results are shown in FIG. 1.

The graph shows the ratios of the gene expressions of each tested substances when the expression ratio of HAS2 or HAS3 to the peptidylprolylisomerase A (PPIA) genes in control (V) after 6 hours of culturing is set to 1.

As a result, it was found that the retinol-modified collagen sustained high expressions of both HAS2 and HAS3 genes for 48 hours or more after culturing. Moreover, it was found that the level of gene expression depended on the concentration of the retinol-modified collagen. On the other hand, it was found that acetic acid retinol ester and palmitic acid retinol ester, both were conventional retinol derivatives, were capable of inducing lower levels of gene expression as compared to the retinol-modified collagen.

Experimental Example 2

Assessment of Effect Affected on Expression of Hyaluronic Acid Synthase Genes

Assessment of Retinol-Modified Collagen Using Keratinocyte Monolayer Culture System 1 (Comparisons with Retinol and Retinol Mixture System)

Figure 2:
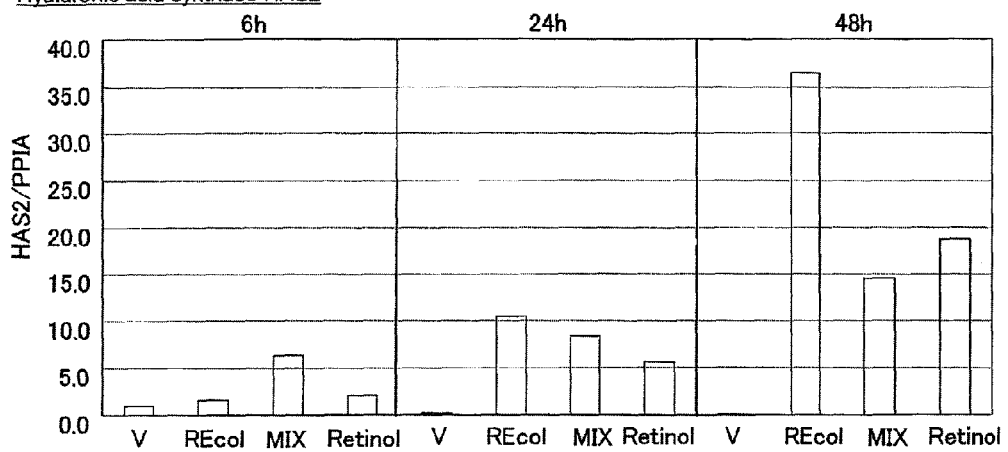
FIG. 2 is a figure showing an effect produced by the retinol-modified collagen of the present invention and an effect produced by a mixture of retinol/collagen derivatives on the expression of the hyaluronic acid synthase genes (HAS2 and HAS3) (Experimental Example 2).
Figure 2:
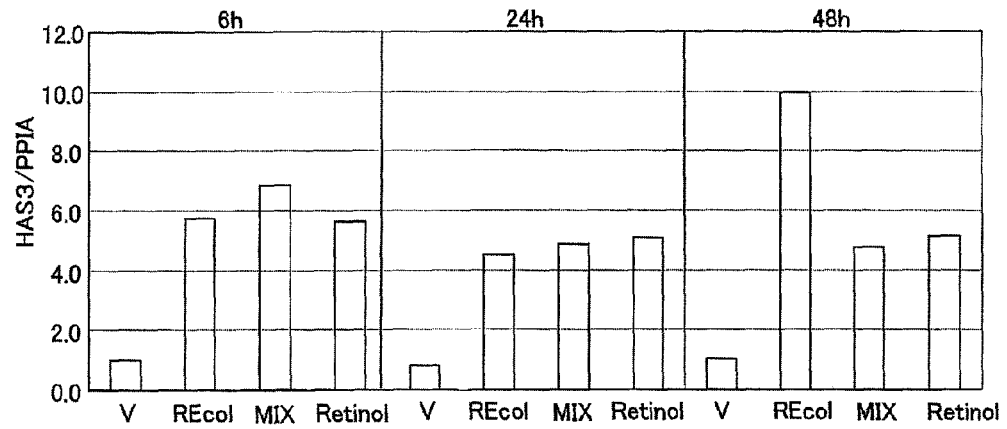

The expressions of hyaluronic acid synthase genes HAS2 and HAS3 were assessed in the same manner as in Experimental Example 1 using a medium prepared to have a final retinol concentration of $10^{-5}$ M, and containing the retinol-modified collagen (REcol) in the preparation example, a mixture (a non-conjugated, MIX) of retinol and the succinic acid-conjugated synthetic collagen in the preparation example, and retinol (Retinol). The results are shown in FIG. 2.

As a result, it was found that the retinol-modified collagen induced remarkably higher expressions of both HAS2 and HAS3 genes after 48 hours from culturing as compared to the mixture of retinol and the succinic acid-conjugated synthetic collagen, and retinol.

Experimental Example 3

Assessment of Cell Toxicity of Retinol-Modified Collagen

The cell survival rates of keratinocytes against retinol-modified collagen were assessed, and were compared with those of the cases where retinol (Sigma Aldrich), a mixture of retinol and synthetic collagen, and acetic acid retinol ester (Sigma Aldrich) which is a general purpose retinol derivative were used, respectively.

Human epidermal keratinocytes (Cell Applications Inc.) were seeded in a 96-well plate containing a human epidermal keratinocytes growth medium (Cell Applications Inc.) so that the number of cells contained in a well was $2.32 \times 10^4$, and were cultured under the condition of 5% $CO_2$-95% air and at 37° C. for about two days until the cells reached confluence.

On the other hand, each of tested substances (retinol (Retinal), retinol-modified collagen (REcol), acetic acid retinol ester (AceRE), and mixture of retinol and synthetic collagen (Retinol+pPHG)) was dissolved in a small amount of dimethylsulfoxide (DMSO), and the medium was diluted with KBM so that the retinol concentration became 5 to 200 µM (or was prepared so that the final DMSO concentration of the medium was 1%, or was diluted with KBM so that the final DMSO concentration was 1% at the control area). Then, this medium replaced the medium which was used for culturing the human epidermal keratinocytes.

Figure 3:
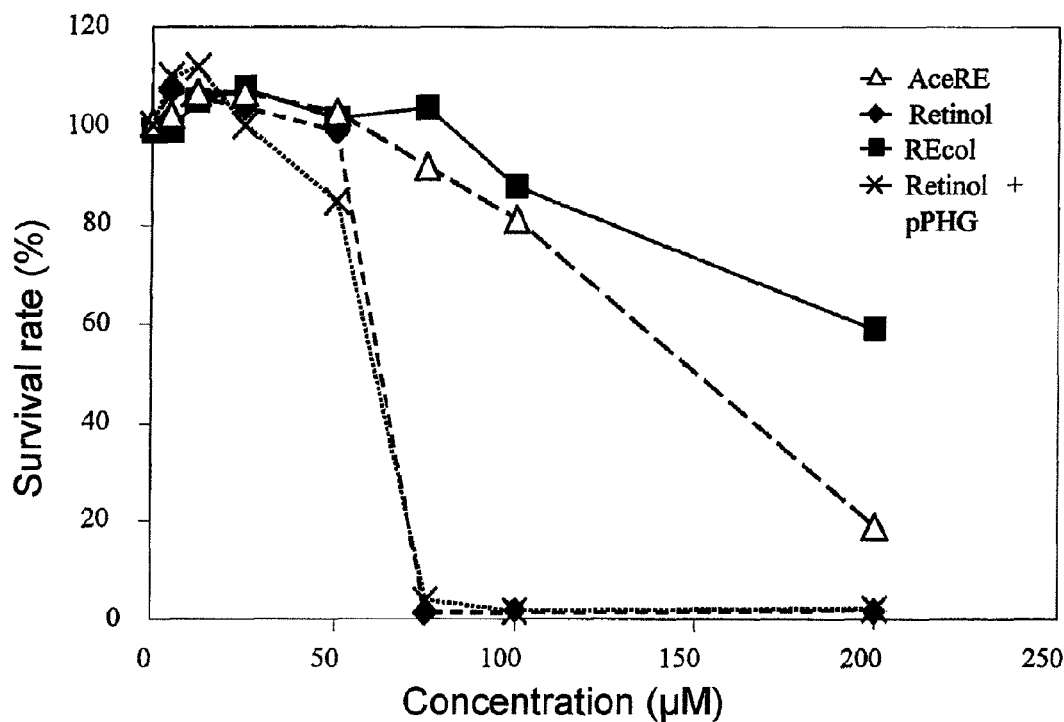
FIG. 3 is a figure showing an effect produced by the retinol-modified collagen of the present invention and an effect produced by a mixture of retinol/collagen on the survivability of human epidermal keratinocytes (Experimental Example 3).

The survival rates of the human epidermal keratinocytes 24 hours after the medium was exchanged were assessed with a cell growth reagent WST-1 (Roche Diagnostics) (N=5). The results are shown in FIG. 3.

As a result, it was shown that the survival rates of the cells were higher when the retinol-modified collagen was used as compared to those of the case where retinol or the mixture of retinol and collagen was used, and that the cell survival rates were the same or higher than those of the case where acetic acid retinol ester was used. Accordingly, it was found that the cytotoxicity of the retinol-modified collagen was as low as that of a general purpose retinol derivative.

Experimental Example 4

Assessment of Inflammatory Cytokine Production of Retinol-Modified Collagen Using Keratinocyte Monolayer Culture System The amount of inflammatory cytokine IL-8 production which is the itch index caused by the retinol-modified collagen in the keratinocyte monolayer culture system was assessed.

Human epidermal keratinocytes (HEK) were seeded in a 24-well plate containing a human epidermal keratinocytes growth medium ($1.0 \times 10^5$ cells/well) and were cultured for two days so that the cells reached confluence.

On the other hand, each of tested substances (retinol (Retinol), retinol-modified collagen (REcol), and succinic acid-conjugated collagen (Suc)) was dissolved in a small amount of DMSO, and the medium was diluted with KBM so that the retinol concentration became $10^{-6}$ M or $10^{-5}$ M (or was prepared so that the final DMSO concentration of the medium was 1%, or was diluted with KBM so that the final DMSO concentration was 1% at the control). Then, this medium replaced the medium which was used for culturing the human epidermal keratinocytes.

Figure 4:
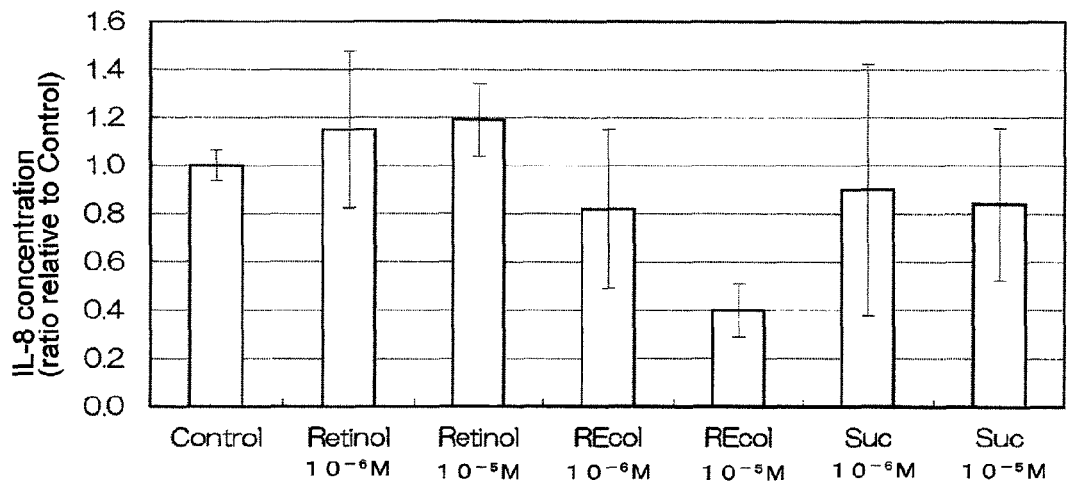
FIG. 4 is a figure showing an effect produced by the retinol-modified collagen of the present invention and an effect produced by collagen derivatives on the amount of IL-8 production in a human epidermal keratinocytes monolayer culture (Experimental Example 4).

The culture medium was recovered 24 hours after the medium was exchanged, and the amount of IL-8 production was quantified with an ELISA kit (R&D Systems) (N=4). The results are shown in FIG. 4.

As a result, it was shown that the production of inflammatory cytokine IL-8 which was considered to be an index for inflammatory disorder of epidermis was suppressed when the retinol-modified collagen was applied as compared to the case where retinol or succinic acid-conjugated collagen was used, and that the retinol-modified collagen could be applied to the skin without causing itches and the like arising as a side effect in using retinol.

Experimental Example 5

Assessment of Inflammatory Cytokine Production of Retinol-Modified Collagen Using Human Three-Dimensional Cultured Epidermis The amount of inflammatory cytokine IL-8 production which is the itch index caused by the retinol-modified collagen in the keratinocyte three-dimensional cultured epidermis system was assessed.

One mL of an accompanying assay medium was added to a 12-well microplate, and human three-dimensional cultured epidermis (LabCyte EPI-Model, J-TEC, LTD.) was cultured in advance under the condition of 5% $CO_2$-95% air and at 37° C. for two hours.

Then, 80 µl of olive oil (Control), retinol (Retinol) prepared to have a retinol concentration of 0.1%, or the retinol-modified collagen (REcol) was added to the cultured epidermis that had been cultured in advance, and the epidermis was cultured for four days. Olive oil was used to prepare the retinol and the retinol-modified collagen solution.

Figure 5:
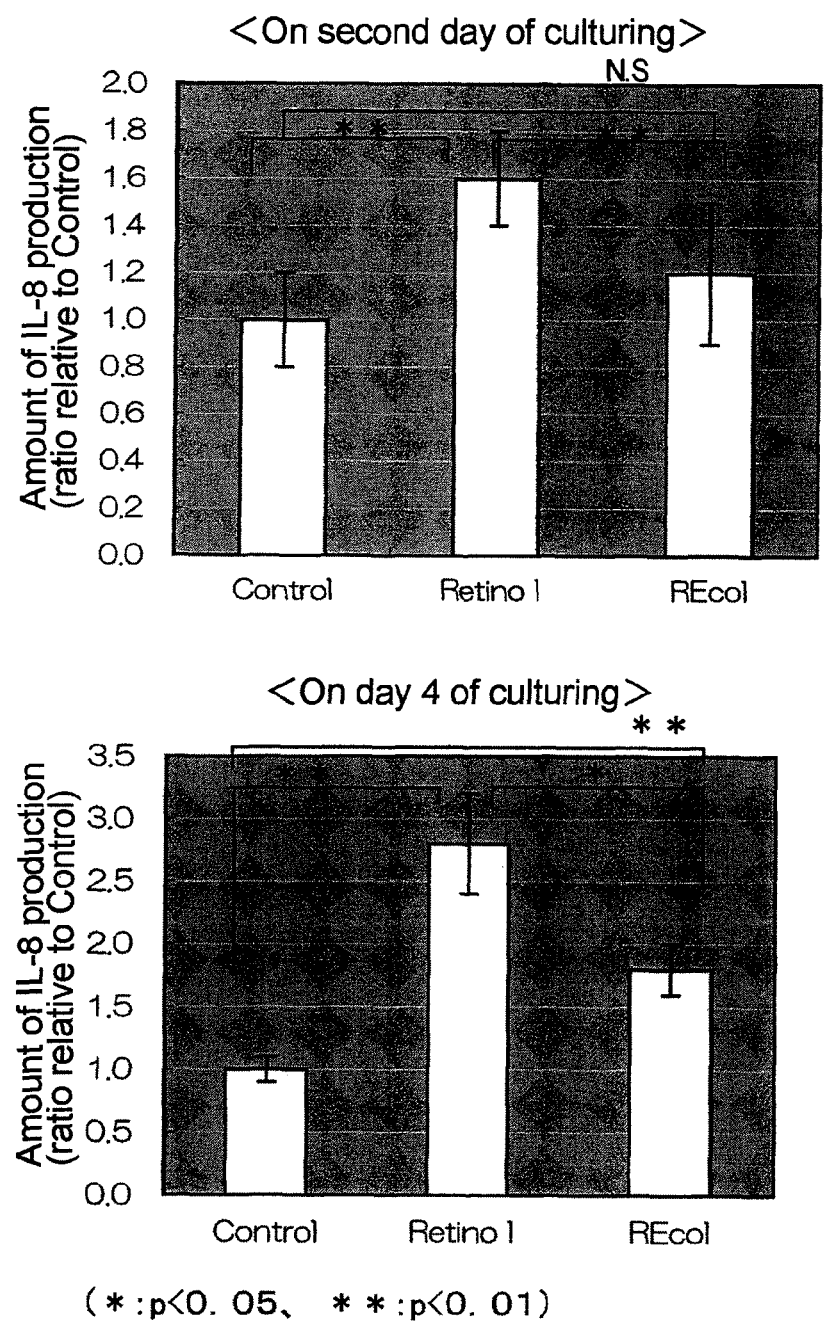
FIG. 5 is a figure showing an effect produced by the retinol-modified collagen of the present invention and an effect produced by retinol on the amount of IL-8 production in human three-dimensional cultured epidermis (Experimental Example 5).

The medium was recovered on the second and fourth days after the addition, and the amount of IL-8 production was quantified with an ELISA kit (R&D Systems) (N=5 until second day, and N=3 until fourth day). The significant difference was analyzed by Student's t-test. The results are shown in FIG. 5.

As a result, it was shown that the production of inflammatory cytokine IL-8 which was considered to be an index for inflammatory disorder of epidermis was suppressed when the retinol-modified collagen was applied as compared to the case where retinol with the same concentration was used, and that the retinol-modified collagen could be applied to the skin without causing itches and the like arising as a side effect in using retinol.

Meanwhile, the amount of IL-8 production caused by the retinol-modified collagen in Experimental Example 4 was more highly suppressed than that of the control area, and also the trend exhibited in Experimental Example 4 was different from the result of Experimental Example 5. The reason for this is considered to arise from the fact that in the case where three-dimensional cultured skin system was used (Experimental Example 5), a substance was added on the stratum corneum so that the area where the substance directly contacted live cells was small, whereas in the case where monolayer culture system was used (Experimental Example 4), the live cells directly contacted the substance so that the effect produced by the substance appeared significantly.

Experimental Example 6

Assessment of Hyaluronic Acid Production by Retinol-Modified Collagen Using Human Three-Dimensional Cultured Epidermis In Experimental Example 1 and Experimental Example 2, it was shown that the retinol-modified collagen induced the expression of hyaluronic acid synthase genes by a real-time PCR assessment of keratinocytes. Thus, as conditions closer to the skin used in real practice, production of hyaluronic acid itself was quantified with human three-dimensional cultured epidermis (LabCyte, EPI-Model 12).

One mL of an accompanying assay medium was added to a 12-well plate, and human three-dimensional cultured epidermis (LabCyte EPI-Model, J-TEC, LTD.) was cultured in advance under the condition of 5% $CO_2$-95% air and at 37° C. for two hours.

Then, 80 µl of olive oil (Control), retinol (Retinol) prepared to have a retinol concentration of 0.1%, or the retinol-modified collagen (REcol) was added to the cultured epidermis that had been cultured in advance, and the epidermis was cultured for four days. Olive oil was used to prepare the retinol and the retinol-modified collagen solution.

Figure 6:
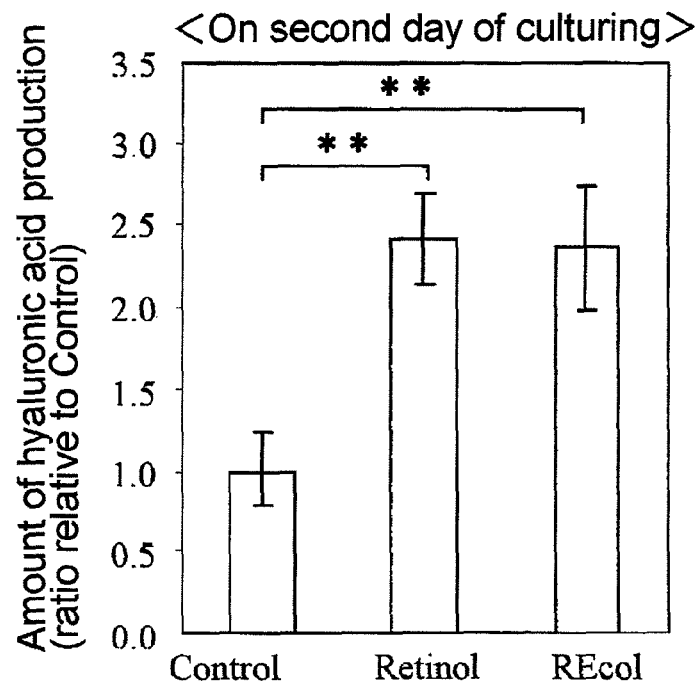
FIG. 6 is a figure showing an effect produced by the retinol-modified collagen of the present invention and an effect produced by retinol on the amount of hyaluronic acid production in human three-dimensional cultured epidermis (Experimental Example 6).
Figure 6:
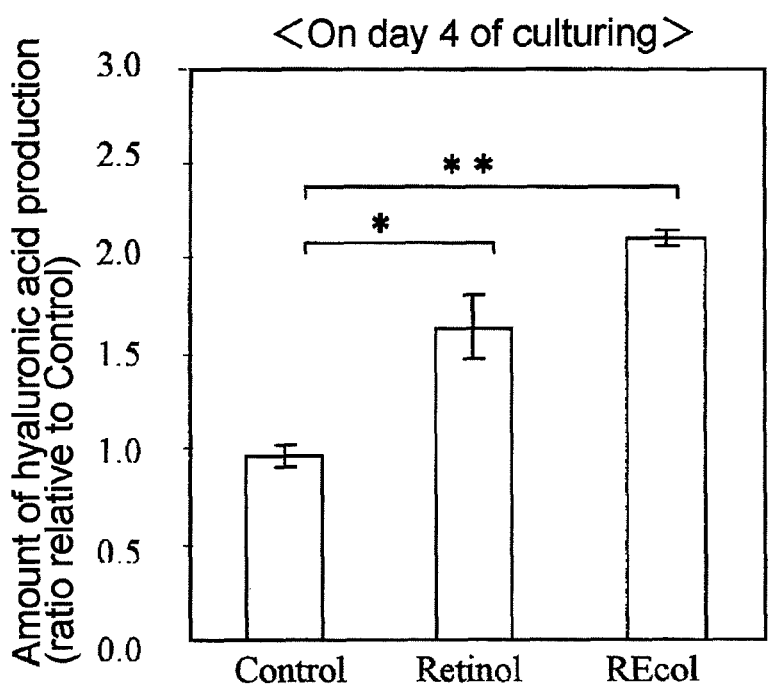

The cultured epidermis medium was recovered on the second and fourth days after the addition, and the amount of hyaluronic acid in the cultured epidermis was quantified with a hyaluronic acid measuring kit (SEIKAGAKU BIOBUSINESS CORPORATION) (N=5 until second day, and N=3 until fourth day). The significant difference was analyzed by Student's t-test. The results are shown in FIG. 6.

As a result, it was shown that the retinol-modified collagen exhibited equivalent hyaluronic acid production amount as retinol on the second day, and exhibited higher hyaluronic acid production amount than retinol on the fourth day.

Experimental Example 7

Assessment of Type-1 Collagen Synthesis by Retinol-Modified Collagen Using Human Three-Dimensional Cultured Skin As conditions closer to the skin used in real practice, the amount of type-1 collagen synthesis was quantified with human three-dimensional cultured skin (EFT-412, KURABO INDUSTRIES, LTD.).

Two mL of an accompanying assay medium was added to a 6-well plate, and human three-dimensional cultured skin (EFT-412, KURABO INDUSTRIES, LTD.) was cultured in advance in an incubator with an atmosphere of 5% $CO_2$ and at 37° C. for one night.

Then, 80 µl of olive oil, 0.5% retinol or 0.5% retinol-modified collagen was added to the cultured skin that had been cultured in advance, and the cultured skin was cultured for two days. Olive oil was used to prepare the retinol and the retinol-modified collagen solution.

Figure 7:
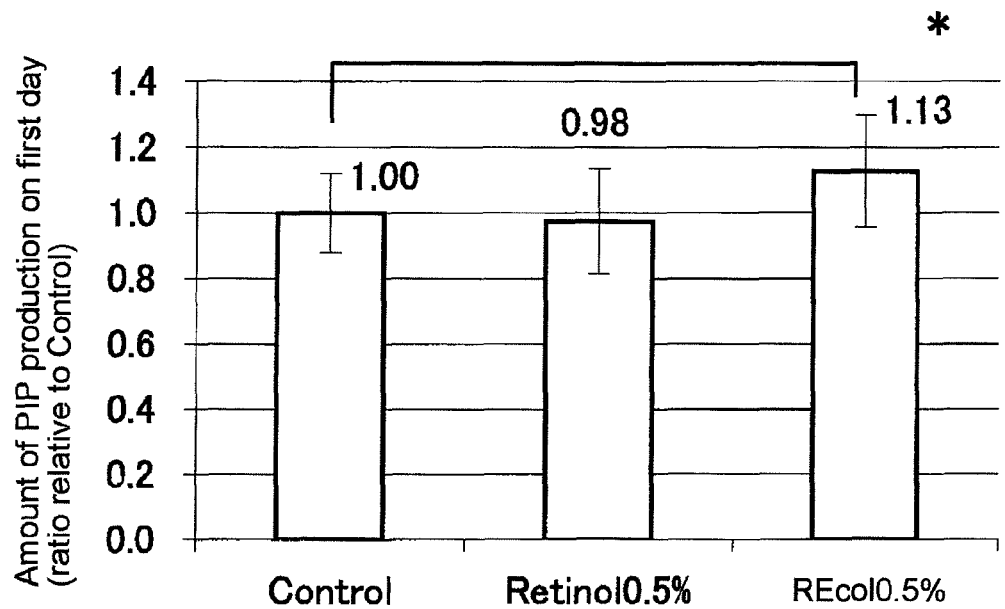
FIG. 7 is a figure showing an effect produced by the retinol-modified collagen of the present invention and an effect produced by retinol on the amount of type-1 collagen synthesis in human three-dimensional cultured epidermis with dermis (Experimental Example 7).
Figure 7:
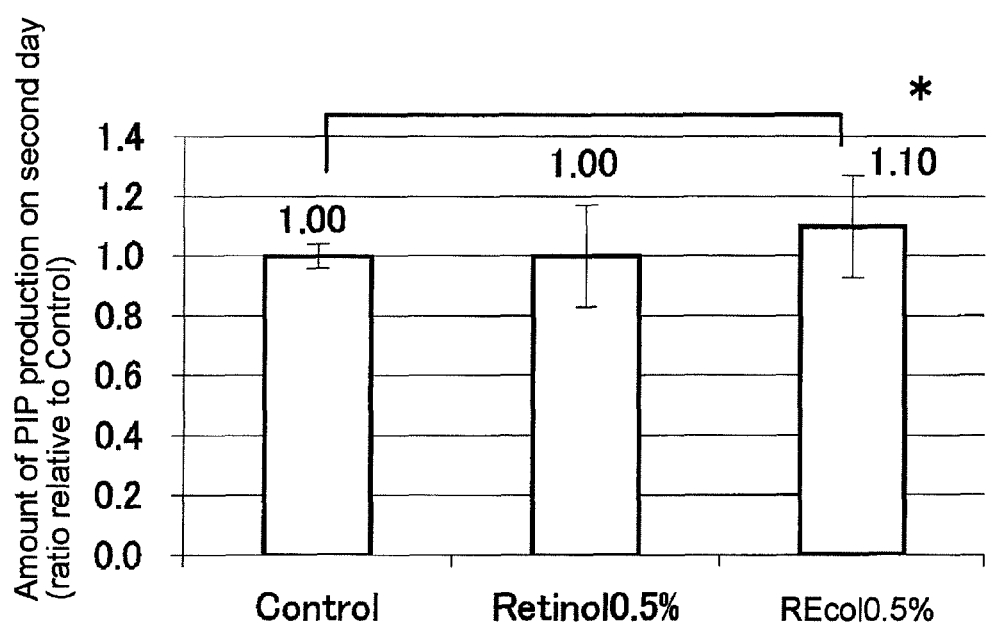

The cultured medium was recovered on the first and second days after the addition, and the amount of type-I procollagen (PIP) in the medium was quantified with a PIP EIA kit (Takara Bio Inc.) (N=6 until second day). The significant difference was analyzed by Student's t-test. The results are shown in FIG. 7.

As a result, the retinol-modified collagen showed higher PIP synthesis amount than that of retinol, and it was confirmed that the retinol-modified collagen exhibited a high promoting effect of type-1 collagen synthesis.

Meanwhile, the retinol-modified collagen of the present invention firmly adsorbs to the skin when applied thereto and permeates the skin to the stratum corneum in a relatively short time, and thus a certain amount of the retinol-modified collagen remains in the skin even when the skin is washed and its effect is sustainably and cumulatively exerted.

Based on these experiments, it was found that the retinol-modified collagen of the present invention sustains high expression of hyaluronic acid synthase genes, and has low cell toxicity, suppression of inflammatory cytokine production, and high hyaluronic acid and collagen production effects over an extended time period as compared to conventional retinol or a retinol derivative. It was shown that the retinol-modified collagen of the present invention when applied to the skin exerts an excellent effect of preventing wrinkle formation, an excellent effect of improving wrinkles, an excellent effect of making the skin beautiful and an excellent effect of improving skin quality.

As mentioned above, it was shown that the retinol-modified collagen of the present invention has an effect, to human skin cells, of enhancing of the amounts of hyaluronic acid production and type-1 collagen production.

Hyaluronic acid exhibits an effect of moisturizing the epidermis due to its water holding capacity, and an effect of improving fine wrinkles formed by drying of the skin and preventing the fine wrinkles from forming by moisturizing the epidermis. In addition, it is reported that hyaluronic acid in the stratum corneum acts as a radical scavenger (Fragrance Journal, 2004, 5, pp. 65-71), and thus the retinol-modified collagen of the present invention has a moisturizing effect, a cell growth effect (turnover prompting effect), and anti-oxidation effect. Moreover, during the course of healing wounds, the amount of hyaluronic acid in the dermis increases and the hyaluronic acid promotes migration and growth of cells, supply of nutrients and enzymes and the like (Fragrance Journal, 2004, 5, pp. 65-71), and thus the retinol-modified collagen of the present invention has a wound healing effect in the epidermis. It is reported that hyaluronic acid in the stratum corneum interacts with an intercellular lipid lamellar structure (The Journal of Investigative Dermatology, 2000, Vol. 114, No. 6, pp. 1184-1187). It is considered that, when hyaluronic acid is added to the cultured skin, the epidermis becomes thick and the hyaluronic acid promotes barrier functions produced by the lipid of the epidermis (Experimental Dermatology, 19, e336-e339). Thus, the retinol-modified collagen of the present invention has an effect of promoting the barrier functions of the epidermis.

Moreover, when dermis collagen increases, an improvement effect of skin elasticity attributed to the dermis structure is produced. Thus, the retinol-modified collagen of the present invention has a prevention/improvement effect on sagging skin, and further has an effect of preventing wrinkle formation and an effect of improving wrinkles on both deep wrinkles in the dermis and shallow wrinkles in the epidermis.

Furthermore, the retinol-modified collagen of the present invention has an effect of improving resiliency of the skin, an effect of improving photo-aged skin, an anti-aging effect, and other efficacies exhibited by cosmetics such as conditioning the skin, conditioning the skin texture, keeping the skin healthy, preventing skin roughness, moisturizing the skin, keeping flexibility of the skin, firming the skin, preventing skin dryness, softening the skin, imparting the skin resiliency, imparting the skin gloss, smoothing the skin and protecting the skin.

Formulation Example 1

Skin Lotion

| Ingredients | Content (%) |
| --- | --- |
| Retinol-modified Collagen | 0.1 |
| Ethanol | 5.0 |
| Glycerin | 4.0 |
| Trehalose | 1.0 |
| Phenoxyethanol | 0.7 |
| PEG-60 Hydrogenated Castor Oil | 0.3 |
| Sodium Hyaluronate | 0.1 |
| Paraben | 0.1 |
| Citric Acid | 0.08 |
| Sodium Citrate | 0.08 |
| Fragrance | 0.03 |
| Purified Water | Balance |
| Total | 100.0 |

Formulation Example 2

Serum

| Ingredients | Content (%) |
| --- | --- |
| Retinol-modified Collagen | 5.0 |
| Ethanol | 10.0 |
| Glycerin | 10.0 |
| 1,3-Butylene Glycol | 6.0 |
| Phenoxyethanol | 0.8 |
| Sodium dl-Pyrroridonnecarboxylate | 0.5 |
| PEG-60 Hydrogenated Castor Oil | 0.5 |
| Xanthan Gum | 0.4 |
| Sodium Hyaluronate | 0.1 |
| Fragrance | 0.1 |
| Paraben | 0.1 |
| Citric Acid | 0.08 |
| Sodium Citrate | 0.08 |
| Purified Water | Balance |
| Total | 100.0 |

Formulation Example 3

Milky Lotion

| Ingredients | Content (%) |
| --- | --- |
| Retinol-modified Collagen | 5.0 |
| 1,3-Butylene Glycol | 12.0 |
| Olive Oil | 8.0 |
| Ethanol | 3.0 |
| Methyl Polysiloxane | 2.0 |
| Stearic Acid | 1.0 |
| Caprylic/Capric Triglyceride | 1.0 |
| Batyl Alcohol | 1.0 |
| Phenoxyethanol | 0.7 |
| Carboxyvinyl Polymer | 0.2 |
| Potassium Hydroxide | 0.2 |
| Lecithin | 0.1 |
| Sodium Hyaluronate | 0.1 |
| Fragrance | 0.1 |
| Paraben | 0.1 |
| Purified Water | Balance |
| Total | 100.0 |

Formulation Example 4

Cream

| Ingredients | Content (%) |
| --- | --- |
| Retinol-modified Collagen | 10.0 |
| Glycerin | 10.0 |
| Olive Oil | 8.0 |
| Squalane | 6.0 |
| Polyglyceryl Monostearate | 4.0 |
| Lipophilic Glyceryl Monostearate | 4.0 |
| Stearic Acid | 4.0 |
| Cetanol | 3.0 |
| Ethanol | 3.0 |
| 1,2-Hexanediol | 1.0 |
| Phenoxyethanol | 0.9 |
| Methyl Polysiloxane | 0.7 |
| Potassium Hydroxide | 0.6 |
| Carboxyvinyl Polymer | 0.2 |
| Fragrance | 0.1 |
| Sodium dl-Pyrroridone carboxylate | 0.1 |
| Paraben | 0.1 |
| Purified Water | Balance |
| Total | 100.0 |

Formulation Example 5

Cream

| Ingredients | Content (%) |
| --- | --- |
| Retinol-modified Collagen | 5.0 |
| Glycerin | 10.0 |
| Olive Oil | 8.0 |
| Squalane | 6.0 |
| Polyglyceryl Monostearate | 4.0 |
| Lipophilic Glyceryl Monostearate | 4.0 |
| Stearic Acid | 4.0 |
| Cetanol | 3.0 |
| Ethanol | 3.0 |
| Phenoxyethanol | 0.9 |
| Methyl Polysiloxane | 0.7 |
| Potassium Hydroxide | 0.6 |
| Carboxyvinyl Polymer | 0.2 |
| Fragrance | 0.1 |
| Sodium dl-Pyrroridone carboxylate | 0.1 |
| Paraben | 0.1 |
| 1,2-Hexanediol | 1.0 |
| Purified Water | Balance |
| Total | 100.0 |

Formulation Example 6

Cleansing Foam

| Ingredients | Content (%) |
| --- | --- |
| Retinol-modified Collagen | 0.1 |
| Myristic Acid | 15.0 |
| Palmitic Acid | 12.0 |
| Stearic Acid | 10.0 |
| Potassium Hydroxide | 8.0 |
| Glycerin | 5.0 |
| 1,3-Butylene Glycol | 4.0 |
| Lauric Acid | 3.0 |
| White Beeswax | 2.0 |
| Ethanol | 2.0 |
| 1,2-Hexanediol | 1.0 |
| Phenoxyethanol | 0.9 |
| Fragrance | 0.6 |
| Disodium Edetate | 0.2 |
| Paraben | 0.1 |
| Purified Water | Balance |
| Total | 100.0 |

Formulation Example 7

Cleansing Gel

| Ingredients | Content (%) |
| --- | --- |
| Retinol-modified Collagen | 0.1 |
| Glycerin | 17.0 |
| Dipropylene Glycol | 17.0 |
| PEG-7 Glyceryl Cocoate | 15.0 |
| Ethanol | 5.0 |
| Olive Oil | 2.0 |
| Carboxyvinyl Polymer | 1.0 |
| Macadamia Nuts Oil | 1.0 |
| Phenoxyethanol | 0.9 |
| Sodium Hydroxide | 0.5 |
| Paraben | 0.1 |
| Fragrance | 0.1 |
| Purified Water | Balance |
| Total | 100.0 |

Formulation Example 8

Make-UP Base

| Ingredients | Content (%) |
| --- | --- |
| Retinol-modified Collagen | 1.0 |
| Decamethyl Cyclopentasiloxane | 45.0 |
| Zinc Oxide | 26.0 |
| 1,3-Butylene Glycol | 5.0 |
| Olive Oil | 3.0 |
| Titanium Oxide | 2.0 |
| Polyglyceryl Monoisostearate | 2.0 |
| Glycerin | 1.0 |
| Ethanol | 1.0 |
| Phenoxyethanol | 0.8 |
| Poly(Oxyethylene/Oxypropylene) Methyl Polysiloxane Copolymer | 0.5 |
| Sodium Chloride | 0.5 |
| Paraben | 0.1 |
| Citric Acid | 0.1 |
| Purified Water | Balance |
| Total | 100.0 |

Formulation Example 9

Powder Foundation

| Ingredients | Content (%) |
| --- | --- |
| Retinol-modified Collagen | 0.1 |
| Sericite | 15.0 |
| Synthetic Fluorphlogopite | 10.0 |
| Titanium Oxide | 10.0 |
| Zinc Oxide | 10.0 |
| Boron Nitride | 5.0 |
| Iron Oxide | 5.0 |
| Bengala | 2.0 |
| Aluminum Oxide | 1.0 |
| Methyl Polysiloxane | 1.0 |
| Methylhydrogen Polysiloxane | 1.0 |
| Cetyl 2-Ethylhexanoate | 1.0 |
| Glyceryl Isostearate | 0.5 |
| Ethanol | 0.1 |
| Paraben | 0.1 |
| Phenoxyethanol | 0.1 |
| Purified Water | 0.1 |
| Sodium Hyaluronate | 0.01 |
| Talc | Balance |
| Total | 100.0 |

Formulation Example 10

Liquid Foundation

| Ingredients | Content (%) |
| --- | --- |
| Retinol-modified Collagen | 0.5 |
| Decamethyl Cyclopentasiloxane | 30.0 |
| Titanium Oxide | 8.0 |
| Zinc Oxide | 5.0 |
| Glyceryl tri(2-ethylhexanoate) | 5.0 |
| 1,3-Butylene Glycol | 5.0 |
| Methyl Polysiloxane Cetylmethyl Polysiloxane Poly(Oxyethylene/Oxypropylene) Methyl Polysiloxane Copolymer | 3.5 |
| Iron Oxide | 3.0 |
| Polyglyceryl Triisostearate | 3.0 |
| 1,2-Pentanediol | 3.0 |
| Sericite | 3.0 |
| Octyl Dodecanol | 2.0 |
| Polyglyceryl Diisostearate | 2.0 |
| Ethanol | 1.0 |
| Sodium Chloride | 0.5 |
| Phenoxyethanol | 0.5 |
| Anhydrous Silicic Acid | 0.1 |
| Purified Water | Balance |
| Total | 100.0 |

Formulation Example 11

Shampoo

| Ingredients | Content (%) |
| --- | --- |
| Retinol-modified Collagen | 0.1 |
| Polyoxyethylene (3 E.O.) Sodium Laurylether Sulfate | 15.0 |
| Propylene Glycol | 8.0 |
| Cocamidopropyl Betaine | 5.0 |
| Coconut diethanolamide | 3.0 |
| Phenoxyethanol | 0.8 |
| Fragrance | 0.7 |
| Paraben | 0.1 |
| Purified Water | Balance |
| Total | 100.0 |

Formulation Example 12

Hair Conditioner

| Ingredients | Content (%) |
| --- | --- |
| Retinol-modified Collagen | 0.1 |
| Caprylic Triglyceride | 5.0 |
| Steartrimonium Chloride | 4.0 |
| Propylene Glycol | 3.0 |
| Polyoxyethylene (5 E.O.) Oleyl Ether | 2.5 |
| Cetanol | 2.5 |
| Phenoxyethanol | 0.8 |
| Fragrance | 0.5 |
| Paraben | 0.1 |
| Purified Water | Balance |
| Total | 100.0 |

Formulation Example 13

Bathing Powder

| Ingredients | Content (%) |
| --- | --- |
| Retinol-modified Collagen | 0.1 |
| Sodium Sulfate | 50.0 |
| Titanium Oxide | 1.0 |
| Fragrance | 0.7 |
| Sodium Hydrogen Carbonate | Balance |
| Total | 100.0 |

Formulation Example 14

Facial Pack

| Ingredients | Content (%) |
| --- | --- |
| Retinol-modified Collagen | Balance |
| Sodium Hyaluronate | 10.0 |
| Total | 100.0 |

INDUSTRIAL APPLICABILITY

The retinol-modified collagen of the present invention may be used as an external composition for the skin or a sheet-shaped cosmetic in the field of pharmaceuticals and, cosmetics.

SEQUENCE TABLE FREE TEXT

SEQ. ID. No: 1 shall be forward primer to apply real-time PCR to hyaluronic acid synthase gene HAS2.

SEQ. ID. No: 2 shall be reverse primer to apply real-time PCR to hyaluronic acid synthase gene HAS2.

SEQ. ID. No: 3 shall be forward primer to apply real-time PCR to hyaluronic acid synthase gene HAS3.

SEQ. ID. No: 4 shall be reverse primer to apply real-time PCR to hyaluronic acid synthase gene HAS3.

What is claimed is:

1. A retinol-modified collagen, comprising a peptide unit represented by formula (2):

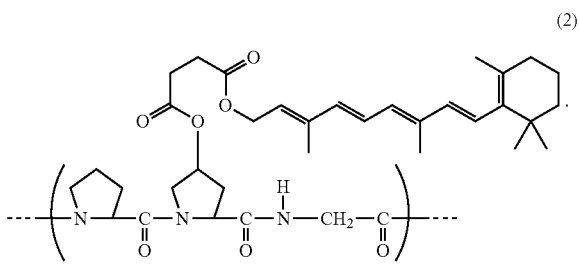

(2)

2. The retinol-modified collagen according to claim 1, wherein the collagen is one or more kinds selected from the group consisting of natural collagen, collagen containing a peptide unit represented by formula (1):

-(A1-A2-Gly)-     (1)

wherein Gly represents glycine, and A1 and A2 represent glycine, proline (Pro) or hydroxyproline (Hyp), provided that at least one of A1 and A2 is Hyp, gelatin, a hydrolysate of natural collagen and a hydrolysate of collagen containing a peptide unit represented by formula (1).

3. The retinol-modified collagen according to claim 1, further comprising at least one peptide unit represented by formula (3):

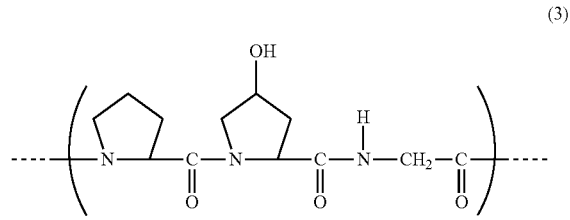

(3)

and a peptide unit represented by formula (4):

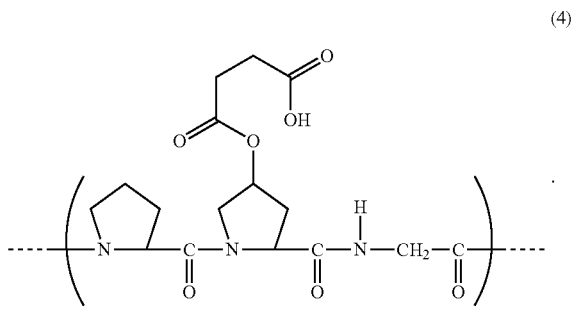

(4)

4. The retinol-modified collagen according to claim 3, wherein a content ratio between the peptide unit represented by formula (2), the peptide unit represented by formula (3) and the peptide unit represented by formula (4) is, in terms of mole ratio, in the range of (2):((3)+(4))=1:99 to 100:0.

5. The retinol-modified collagen according to claim 1, wherein the peak of molecular weight distribution falls within the range of molecular weight of 500 to 1,000,000.

6. The retinol-modified collagen according to claim 1, which is an agent for suppressing wrinkle formation.

7. The retinol-modified collagen according to claim 1, which is a hyaluronic acid production accelerator.

8. The retinol-modified collagen according to claim 1, which is an activating agent for hyaluronic acid synthase.

9. The retinol-modified collagen according to claim 1, wherein the retinol-modified collagen is a collagen production accelerator.

10. A method for producing the retinol-modified collagen according to claim 1, comprising:
   (1) preparing a succinic acid-conjugated collagen by attaching a succinic acid or its anhydride to at least one hydroxyl group of collagen; and then
   (2) attaching retinol to a carboxyl group of the succinic acid of the succinic acid-conjugated collagen.

11. The method for production according to claim 10, wherein the collagen is one or more kinds selected from the group consisting of natural collagen, collagen containing a peptide unit represented by formula (1):

-(A1-A2-Gly)-     (1)

wherein Gly represents glycine, and A1 and A2 represent glycine, proline (Pro) or hydroxyproline (Hyp), provided that at least one of A1 and A2 is Hyp, gelatin, a hydrolysate of natural collagen and a hydrolysate of collagen containing a peptide unit represented by formula (1).

12. The method for production according to claim 10, wherein a tertiary amine is used as a solvent in step (2).

13. The method for production according to claim 12, wherein the tertiary amine is a trialkylamine.

14. The method for production according to claim 13, wherein the trialkylamine is diisopropylethylamine.

15. An external composition for the skin comprising, as an active ingredient, the retinol-modified collagen according to claim 1.

16. An external composition for the skin comprising the retinol-modified collagen according to claim 1 in an amount of 0.00001 to 30% by weight based on the amount of the whole composition.

17. The external composition for the skin according to claim 15, which is used for suppressing wrinkle formation.

18. A sheet-shaped cosmetic comprising the retinol-modified collagen according to claim 1.

* * * * *